United States Patent
Gunasekaran et al.

(10) Patent No.: US 7,614,304 B2
(45) Date of Patent: Nov. 10, 2009

(54) ULTRASONIC TESTING SYSTEM AND METHOD FOR CERAMIC HONEYCOMB STRUCTURES

(75) Inventors: Natarajan Gunasekaran, Painted Post, NY (US); Zhiqiang Shi, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 344 days.

(21) Appl. No.: 11/708,896

(22) Filed: Feb. 21, 2007

(65) Prior Publication Data
US 2007/0266790 A1  Nov. 22, 2007

(51) Int. Cl.
*G01N 29/06* (2006.01)
(52) U.S. Cl. .............................. 73/598; 73/600; 73/602
(58) Field of Classification Search .................. 73/597, 73/598
See application file for complete search history.

(56) References Cited

U.S. PATENT DOCUMENTS

| | | | | |
|---|---|---|---|---|
| 3,732,444 | A | * | 5/1973 | Miller ........................... 73/644 |
| 3,813,926 | A | | 6/1974 | Stubbeman ................... 73/609 |
| 4,319,840 | A | | 3/1982 | Kondo et al. ................. 356/241 |
| 4,558,598 | A | * | 12/1985 | Young ........................... 73/644 |
| 4,651,566 | A | * | 3/1987 | Andersson et al. ............. 73/589 |
| 4,752,895 | A | | 6/1988 | Sarr ............................. 702/39 |
| 4,766,554 | A | * | 8/1988 | Sarr et al. ...................... 702/39 |
| 4,869,944 | A | | 9/1989 | Harada et al. ................. 428/116 |
| 5,056,368 | A | | 10/1991 | Kawasaki et al. ............. 73/642 |
| 5,062,911 | A | | 11/1991 | Hampton et al. ........... 156/89.14 |
| 6,367,330 | B1 | | 4/2002 | Schafer ......................... 73/598 |
| 6,372,677 | B1 | | 4/2002 | Nose et al. ................... 501/119 |

(Continued)

FOREIGN PATENT DOCUMENTS

JP  63-263467  10/1988

(Continued)

OTHER PUBLICATIONS

Peters et al., "Resonant Transmission of Air-Coupled Ultrasound Through Metallic Inserts in Honeycomb Sandwich Structures", CP760, Review of Quantitative Nondestructive Evaluation, vol. 24, 2005 American Institute of Physics, 0-7354-0245-0/05, pp. 1026-1032.

(Continued)

*Primary Examiner*—Hezron Williams
*Assistant Examiner*—Rose M Miller
(74) *Attorney, Agent, or Firm*—Matthew B. McNutt

(57) ABSTRACT

Both a system and method for detecting the presence or absence of internal discontinuities or inhomogeneities in a fired or green ceramic honeycomb structure is provided. The system includes a membrane disposed over a surface of the honeycomb structure, at least one ultrasonic transmitter that engages the membrane and transmits ultrasonic waves into the honeycomb structure, a translation assembly connected to the ultrasonic transmitter for sliding said transmitter across said membrane in a predetermined pattern, and an ultrasonic receiver that receives a modulated response from the ultrasonic waves transmitted into the honeycomb structure. The membrane is preferably plastic sheet material, such as polyester, having a temporary adhesive on one side and a thickness that is about one-quarter of the wavelength of the ultrasonic waves in order to avoid attenuation of the modulated response. In the method, the plastic sheet material is applied over the surface of the honeycomb structure via the temporary adhesive and the ultrasonic transmitter is simultaneously actuated while the translation assembly continuously slides the ultrasonic transmitter over the plastic sheet material in a predetermined scanning pattern.

22 Claims, 16 Drawing Sheets

U.S. PATENT DOCUMENTS

| | | | |
|---|---|---|---|
| 6,457,363 B1 | 10/2002 | Schafer | 73/596 |
| 6,666,070 B1 | 12/2003 | Hagg et al. | 73/38 |
| 6,840,083 B2 | 1/2005 | Hijikata | 73/12.01 |
| 6,843,130 B2 | 1/2005 | Georgeson | 73/600 |
| 6,945,111 B2 * | 9/2005 | Georgeson | 73/600 |
| 6,964,694 B2 | 11/2005 | Rauchfuss et al. | 95/1 |
| 7,012,678 B2 | 3/2006 | Enomoto et al. | 256/237.1 |
| 7,276,101 B2 | 10/2007 | Ichikawa | 55/523 |
| 2002/0039964 A1 | 4/2002 | Tanaka et al. | 502/304 |
| 2005/0247131 A1 | 11/2005 | Breuer | 73/579 |
| 2006/0112767 A1 * | 6/2006 | Obrachta | 73/596 |
| 2006/0266123 A1 * | 11/2006 | Georgeson et al. | 73/634 |
| 2007/0144260 A1 | 6/2007 | Fei et al. | 73/596 |
| 2007/0199380 A1 | 8/2007 | Daoud | 73/596 |
| 2007/0266789 A1 | 11/2007 | Hampton et al. | 73/596 |

FOREIGN PATENT DOCUMENTS

| | | |
|---|---|---|
| JP | 7-244026 | 9/1995 |
| JP | 2006/106011 | 4/1996 |
| JP | 2004-151078 | 5/2004 |
| WO | 2005/095932 | 10/2005 |

OTHER PUBLICATIONS

Sun et al., "NDT Technologies for Ceramic Matrix Composites: Oxide and Nonoxide", Submitted Oct. 2005, Materials Evaluation, Jan. 2006, pp. 52-60.

M. Asmani et al, "Influence of porosity on Young's modulus and Poisson's ration in alumina ceramics", Journal of the European Ceramic Society, vol. 21 (2001), pp. 1081-1086.

Hyunjo Jeong et al, "Quantitative estimation of material properties of porous ceramics by means of composite micromechanics and ultrasonic velocity", NDT&E International, vol. 29, No. 2, 1996, pp. 95-101.

L.P. Martin et al, "Effect of particle size distribution upon specific surface area and ultrasonic velocity in sintered ceramic powders", Materials Science and Engineering, vol. A246 (1998), pp. 151-160.

A.K. Mukhopadhyay et al, "An analysis of microstructural parameters in the minimum contact area model for ultrasonic velocity-porosity relations", Journal of the European Ceramic Society, vol. 20 (2000), pp. 29-38.

Byoung-Chul Shin et al, "Ultrasonic transducers for continuous-cast billets", Sensors and Actuators, vol. A51 (1996), pp. 173-177.

Alexander Wanner, "Elastic modulus measurements of extremely porous ceramic materials by ultrasonic phase spectroscopy", Materials Science and Engineering, vol. A248 (1998), pp. 35-43.

L.-S. Chang et al, "Characterization of alumina ceramics by ultrasonic testing", Materials Characterization, vol. 45 (2000), pp. 221-226.

* cited by examiner

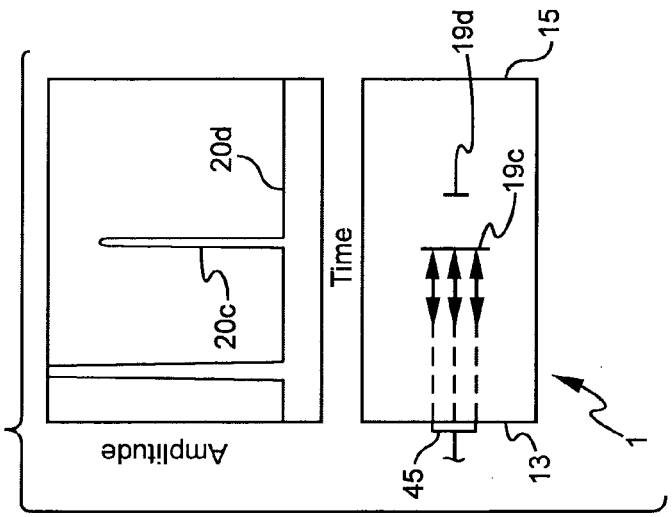
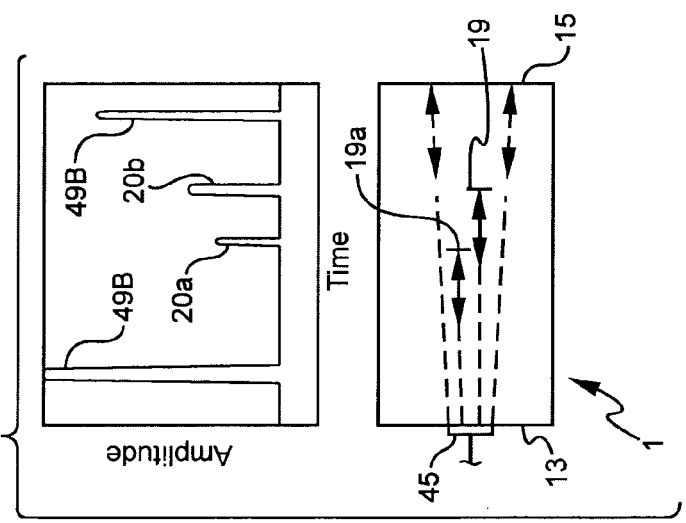
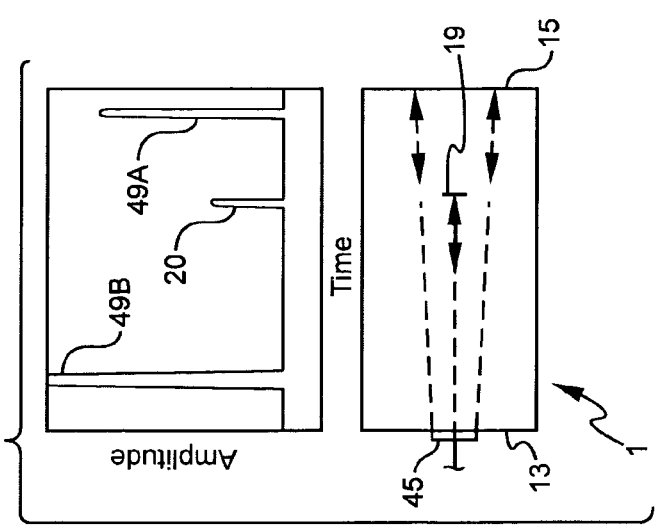

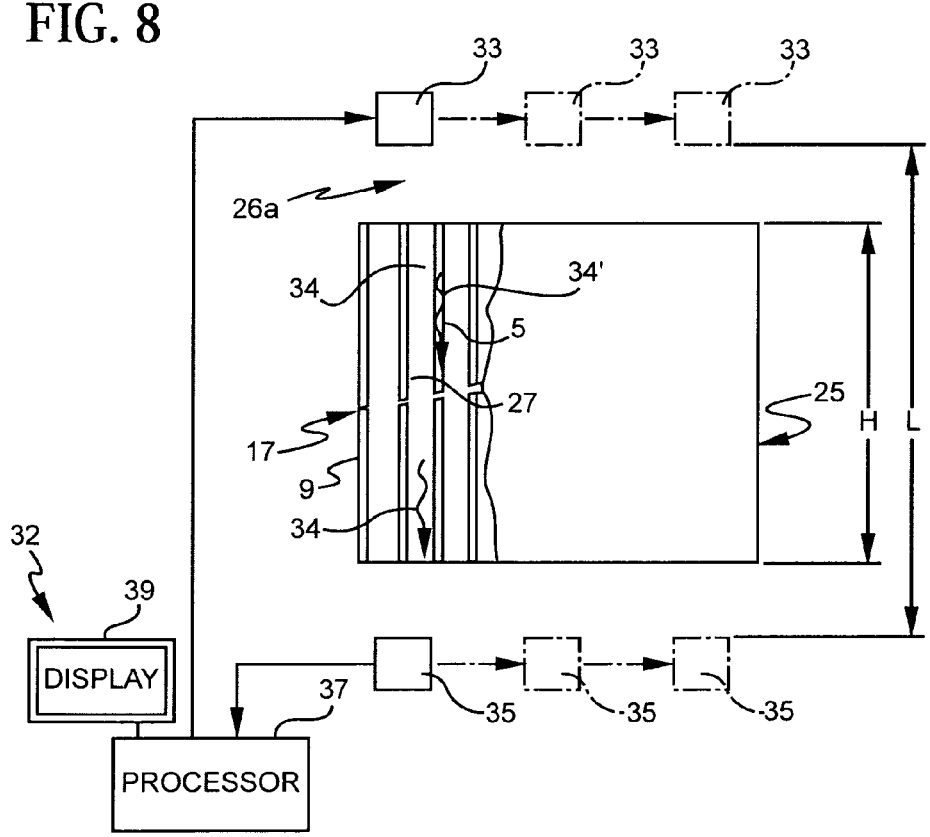

Multiple B-scans

Raster C-scan

ULTRASONIC TESTING SYSTEM AND METHOD FOR CERAMIC HONEYCOMB STRUCTURES

CROSS-REFERENCE TO RELATED APPLICATIONS

This application claims priority to, and the benefit of, U.S. patent application Ser. No. 11/435,666 entitled "Pulse Echo Ultrasonic Testing Method for Ceramic Honeycomb Structures" filed May 16, 2006.

FIELD OF THE INVENTION

This invention generally relates to the detection of internal discontinuities in ceramic honeycomb structures, and is specifically concerned with an ultrasonic testing system and method that quickly and efficiently determines presence or absence of internal discontinuities within such structures.

BACKGROUND OF THE INVENTION

Ceramic honeycomb structures are used in vehicular exhaust systems to reduce pollutants. Such structures generally comprise a network of interconnected web walls that form a matrix of elongated, gas-conducting cells which may be square, octagonal or hexagonal in shape for example. The network of web walls is surrounded by a cylindrical outer skin that is integrally connected to the outer edges of the web walls to form a can- or oval-shaped structure having opposing inlet and outlet ends for receiving and expelling exhaust gases through the matrix of cells.

Such ceramic honeycomb structures may be used as either particulate filters in the exhaust systems of diesel-powered automobiles or other equipment, or as automotive catalytic converters. When used as particulate filters, the open ends of the cells on the inlet and outlet ends of the structure are preferably plugged in "checkerboard" fashion such that exhaust gases entering the inlet end of the structure must pass through the porous, ceramic web walls before they are allowed to exit the open ends of the cells at the outlet end of the structure. When used as catalytic converters, the cells remain unplugged so that the exhaust gases may flow directly through them, and the cell walls are coated with a precious metal catalyst containing platinum, rhodium, or palladium, for example. After the web walls reach a required light-off temperature, the catalyst impregnated over the web walls oxidizes $CO_2$, and disassociates $NO_x$ into $N_2$ and $O_2$. Both applications of ceramic honeycomb structures are important in reducing pollutants that would otherwise be expelled into the environment.

Such ceramic structures are formed by extruding a paste-like, ceramic precursor to cordierite, mullite, silicon carbide, or aluminum titanate through a die to simultaneously form the network of web walls preferably along with the integrally-connected outer skin. The resulting extruded, green body is cut, dried and moved to a kiln which converts the green ceramic body into a fired ceramic body. The fired body may then either be plugged in the aforementioned pattern to form a diesel particulate filter, or subjected to a catalyst wash coat in order to impregnate the walls of the flow-through cells with the catalyst.

Unfortunately, during the extrusion, handling and firing procedures, internal damage can occur within the ceramic substrate which can significantly compromise the performance of the body in removing pollutants from the automotive exhaust system where it ultimately resides. Such damage can include cracks oriented along the axis of rotation of the structure and cracks transverse to this axis, referred to hereinafter as axial cracks and "ring-off" cracks, respectively. Still other damage is manifested by a localized separation between the network of web walls, and the outer skin of the structure. Finally, external hairline cracks on the surface of the structure can occur, and possibly other strength-compromising scratches; and deformities.

Systems and methods for testing various manufactured parts for discontinuities are also known in the prior art, such as x-ray and CT systems that scan such manufactured parts with x-rays or other types of radiation. However, such x-ray inspections are insensitive to the internal cracks which may exist within honeycomb ceramic structures unless the defect is larger than a certain size. Even when the defect is sufficiently large to be detected, the x-ray image must be examined carefully for fine details in order to discern such defects. The time to completely inspect one honeycomb structure can take hours, which is far too long to be used in connection with a practical manufacturing process. Other techniques based on the same principle as an x-ray inspection, such as laminography and tomography suffer from the same drawbacks, in that they require far too much time and effort to be able to effectively and reliably detect cracks and other discontinuities within a time frame suited to a practical manufacturing process.

Clearly, what is needed is a method for inspecting ceramic honeycomb structures which is capable of quickly and reliably detecting the presence or absence of such discontinuities as axial or "ring-off cracks", skin separations, hairline cracks on the exterior, and/or other deformities or faults that could compromise the function of the ceramic structure in an exhaust system. Ideally, such a method would be quick, non-invasive and well-suited for incorporation into standard manufacturing processes. Finally, it would be desirable if such a method were applicable both to green or fired ceramic structures so that the inspection method could be used both to obviate the need for firing defective green bodies, as well as to provide a final check as to the finished, fired product.

SUMMARY OF THE INVENTION

Generally speaking, the invention is both a system and a method for ultrasonically detecting internal discontinuities and inhomogeneities in a green or fired ceramic honeycomb structure that overcomes or at least ameliorates the problems associated with the prior art. To this end, the system of the invention comprises a membrane disposed in contact with a surface of the honeycomb structure, at least one ultrasonic transmitter that slidably engages the membrane and transmits ultrasonic waves into the honeycomb structure, a translation assembly connected to the ultrasonic transmitter for slidably moving the transmitter across the membrane in a predetermined pattern, and an ultrasonic receiver receives a modulated response from the ultrasonic waves transmitted into the honeycomb structure. The system may further include a digital processor connected to both the translation assembly and the ultrasonic transmitter for coordinating the actuation of the ultrasonic transmitter while the translation assembly continuously moves the transmitter, thereby greatly expediting the inspection process over "stop and go" techniques where the ultrasonic transmitter must come to a complete stop prior to every actuation. Finally, the system preferably includes the application of a gel coupling compound over the membrane to facilitate slidable movement and acoustical coupling to the ceramic structure.

The membrane is preferably a flexible sheet material that includes a sheet of plastic having a temporary adhesive on one side such that the flexible sheet material may be detachably adhered on the surface of the honeycomb structure. Additionally, in order to avoid attenuation of the modulated response from the transmission of the ultrasonic waves, the sheet material an acoustic impedance that is within about 20% of the geometric mean of the acoustic impedance of the ceramic honeycomb structure and the ambient air, and has a thickness that is approximately one quarter of the wavelength of the ultrasonic waves transmitted by the ultrasonic transmitter. In the preferred embodiment, the plastic sheet is a less than five-mil thick sheet, such as sheet of polyester having a layer of temporary adhesive applied to one side. Two-mil thick adhesive backed polyester sheet works acceptably.

The method of the invention generally includes the steps of applying the membrane in contact with a surface of the honeycomb structure, slidably moving the ultrasonic transmitter over the membrane while simultaneously transmitting ultrasonic waves into the honeycomb structure, and receiving a response of the transmitted ultrasonic wave as modulated by the structure. When the membrane is a flexible sheet material that includes a sheet of plastic having a temporary adhesive on one side, the membrane is applied over the surface of the honeycomb structure by simply lightly pressing it over the surface to remove air pockets. A gel coupling compound is then applied over the membrane. The ultrasonic transmitter is simultaneously operated in a pulse echo mode while the translation assembly moves it in a predetermined-pattern over the membrane. The predetermined pattern may take the form of either a raster scan, or multiple linear scans over the surface of the ceramic structure. Multiple ultrasonic transmitters may be used in order to expedite the scanning process. The honeycomb ceramic structure may be formed from cordierite, aluminum titanate, or mullite, and the frequency of the ultrasonic waves transmitted by the transmitter may be from between about 200 kHz to 1 MHz. When the honeycomb ceramic structure is formed from cordierite, the frequency of the ultrasonic waves is preferably between about 200 kHz and 600 kHz. The digital processor filters out noise from the response signals in order to determine whether or not discontinuities or in homogenize these are present. At the last step of the scanning method, the membrane is removed by simply peeling it off of the side of the honeycomb structure scanned.

DESCRIPTION OF THE DRAWINGS

FIGS. 5A, 5B and 5C illustrate the amplitude over time graphs of pulse echo's reflected in a ceramic substrate having a single small crack, two small cracks and two cracks wherein the signature of the second crack is masked, respectively;

FIG. 8 is a partial cross-sectional diagram of the embodiment of the non-contact test apparatus of FIG. 7.

DETAILED DESCRIPTION OF THE PREFERRED EMBODIMENT

Figure 1A:
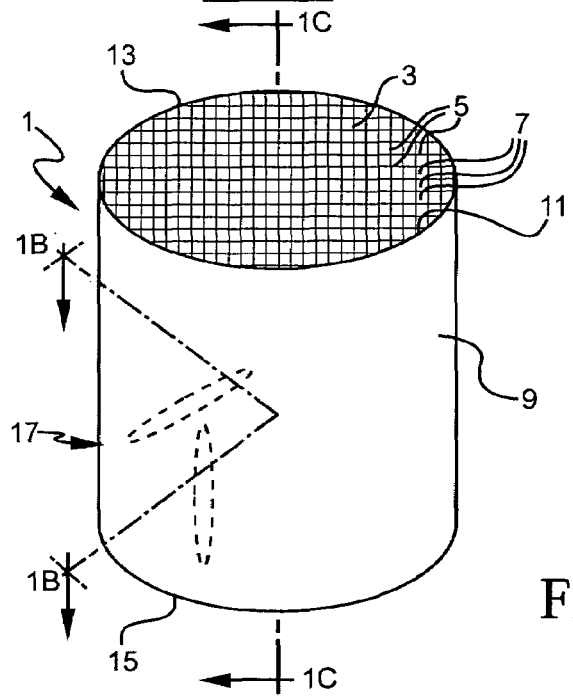
FIG. 1A is a perspective view of a prior art catalytic, flow-through ceramic substrate having internal discontinuities.
Figure 1B:
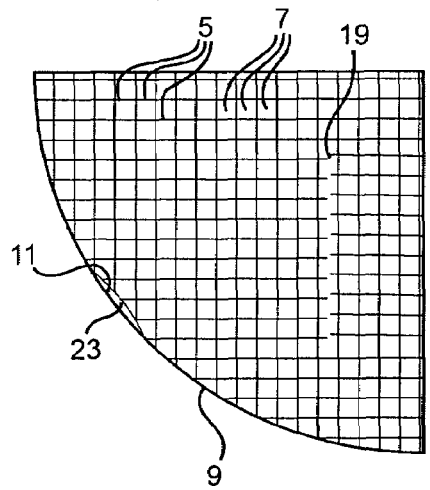
FIG. 1B is a plan, partial (¼ section) view of the ceramic substrate of FIG. 1A along the line 1B-1B.
Figure 1C:
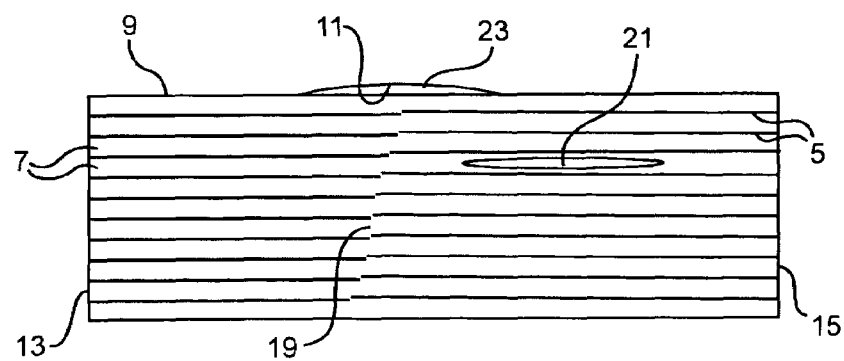
FIG. 1C is a partial side cross-sectional view of the ceramic substrate of FIG. 1A along the line 1C-1C.

With reference now to FIGS. 1A, 1B and 1C, both the method and the device of the invention are particularly useful in detecting discontinuities and other inhomogenieties which may be present in a ceramic honeycomb structure 1 of the type used in diesel and automotive exhaust systems. Such structures include a network 3 of web walls 5 that define gas-conducting cells 7 along the axis of rotation of the structure 1. The network 3 of web walls 5 is surrounded by an outer skin 9. The outer skin 9 has an inner edge 11 that is generally integrally connected (except, for example, at defects) to the outer edges of the network 3 of walls 5, as is best seen in FIG. 1B. The resulting can-shaped structure has an inlet end 13 for receiving exhaust gases from a diesel engine or automobile engine, and an outlet end 15 for expelling these gases.

Ceramic honeycomb structures 1 used as flow-through catalyst substrates have cells 7 which are completely open between the inlet and outlet ends 13, 15. The density of the cells 7 may be between approximately 100-900 cells per square inch, for example. Cell density may be maximized in order to maximize the area of contact between the automotive exhaust gases which blow directly through the gas conducting cell 7, and the web walls 5. To reduce the pressure drop that the flow-through substrate 1 imposes on the exhaust gases, the web walls 5 are typically rendered quite thin, i.e. on the order of 2-10 mils, or even 2-6 mils.

When such honeycomb structures 1 are used as wall-flow filters, such as diesel particulate filters, the open ends of the cell 7 at the inlet and outlet ends 13, 15 are plugged in a "checkerboard" pattern to force the diesel exhaust gases to pass through the porous web walls 5 before exiting the outlet end 15. The density of the cells 7 is lower than in substrates used as catalytic character, i.e. typically between about 100 and 400 cells per square inch, for example, and the web walls 5 are generally thicker, on the order of 10-25 mils thick, or even 12-16 mils thick, for example. Whether the structure 1 is used as a catalytic carrier or a particulate filter, the outer skin 9 is approximately four times as thick as the web walls 5.

Such structures 1 are manufactured by extruding a plasticized ceramic forming precursor of cordierite, mullite, silicon carbide or aluminum titanate through an extrusion die. The extruded "green body" is then cut and dried. Such green bodies are quite fragile, and must be transported to a kiln, where the resultant heat transforms the relatively soft and fragile green body into a hardened, fired honeycomb.

Unfortunately, the extrusion process and the subsequent necessary handling or processing (including cutting and firing) of the resulting, fragile green body can cause discontinuities and inhomogenieties 17 to occur in the interior of the structure 1. Even after the green body is fired, the relatively thin, brittle walls of the honeycomb structure can crack in response to mechanical shock and pressure. Such discontinuities 17 may include ring-off cracks 19 which are oriented transverse to the axis of rotation of the structure 1, and axial cracks 21 which are oriented parallel to this axis. Additionally, separations 23 can occur between the outside edges of the network 3 of web walls 5, and the inner edge 11 of the outer skin 9 can also occur. When the resulting structure 1 is used as a particulate filter, such discontinuities 17 may allow exhaust gases to flow completely through the structure 1 without filtration. When the structure 1 is used as a catalytic carrier, such discontinuities 17 form localized areas of rapid flow that may bypass the catalytic breakdown of pollutants in the exhaust. Inhomogenieties include dimensional variations (geometry related such as wall thickness variations within the interior of the substrate, wall orientation and/or waviness), and microstructural variations such as density differences, variations in porosity, and variations in amounts of microcracking within the structure.

Figure 2A:
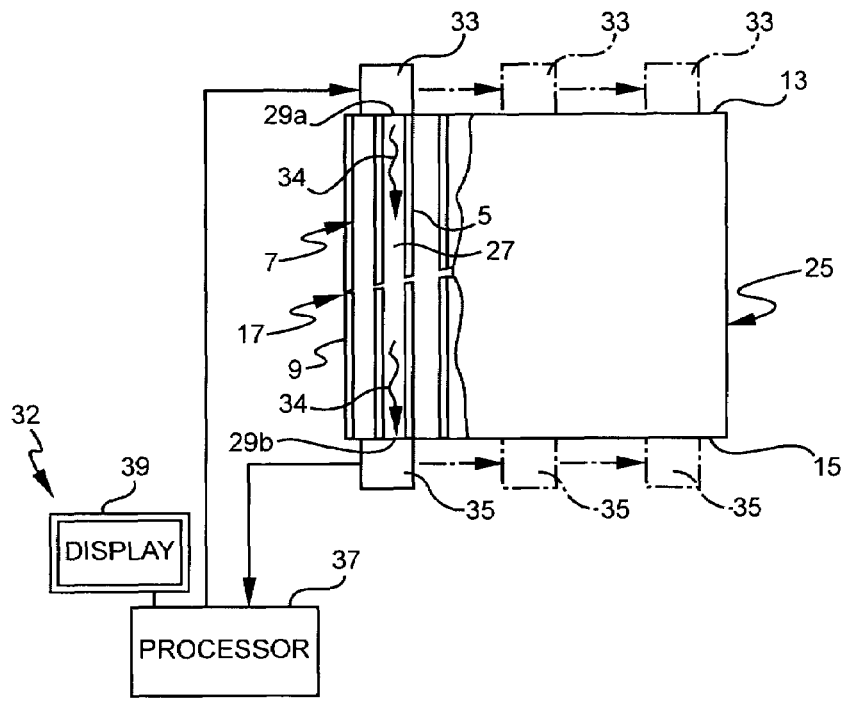
FIG. 2A is a schematic diagram of the application of the contact through-transmission ultrasonic testing method of the invention as applied to a flow-through ceramic substrate.

FIG. 2A illustrates a first embodiment of the method of the invention, as applied to a flow-through ceramic structure 25 whose cells 7 define air passageways 27 having open ends 29a, 29b at both the inlet and outlet ends 13, 15. This mode is referred to herein as a "contact through-transmission" method. In this embodiment of the method, an ultrasonic signal is sent through the web walls 5 extending between the inlet and outlet ends 13, 15. For this purpose, an ultrasonic testing device 32 is provided having a transmitting transducer 33 for transmitting ultrasonic waves 34 (designated by wavy arrows), and a receiving transducer 35 for receiving the waves 34. In this embodiment of the method, the transmitting and receiving transducers 33, 35 are maintained in opposing relationship, and in contact with the structure 25, and periodically re-located and re-actuated across the inlet and outlet ends 13, 15 of the substrate 25 such that the receiving transducer 35 periodically receives directly transmitted ultrasonic waves 34 from the transmitting transducer 33. Each time, the transducers 33, 35 are substantially directly aligned across the structure from each other. Both the transmitting and receiving transducers 33, 35 may be piezo-electric transducers of the type well known in the art. The receiving piezo-electric transducer 35 resonates in response to the ultrasonic signal 34 transmitted from the transmitting transducer 33, which causes it to generate an electric signal. This signal is in turn conducted to a digital processor 37. The digital processor 37 filters the noise in the signal 34 received by the receiving transducer 35 resulting from reflections of the ultrasonic waves 34 between the transducers 33, 35, and sends the filtered signal to a display 39. Alternatively, other suitable ultrasonic testing transducers may be employed.

The resulting combined outputs of the transmitting and receiving transducer produces a kind of linear scan across the diameter or a chord of the substrate 25. When the substrate 25 is a flow-through substrate as illustrated in FIG. 2A, the transducers 33, 35 may be actuated when the transmitting transducer 33 is directly over one of the longitudinal web walls 5 such that the wave 34 is conducted through the substrate itself.

Preferably, the ultrasonic waves 34 generated by the transmitting transducer 33 are less than about 5 MHz in frequency. More preferably, the frequency of the ultrasonic waves 34 for the contact through-transmission method are between about 150 and 700 KHz, and most preferably between 150 and 500 KHz. The applicants have found that when the ultrasonic waves 34 are generated within such ranges, the signal-to-noise ratio is maximized. By contrast, when higher-frequency ultrasonic radiation is used, the applicants found that the inherent porosity of the material forming the substrate 25 makes it difficult, if not impossible to resolve discontinuity 17 located in the interior of the structure 1 due the large resulting noise factor.

Figure 2B:
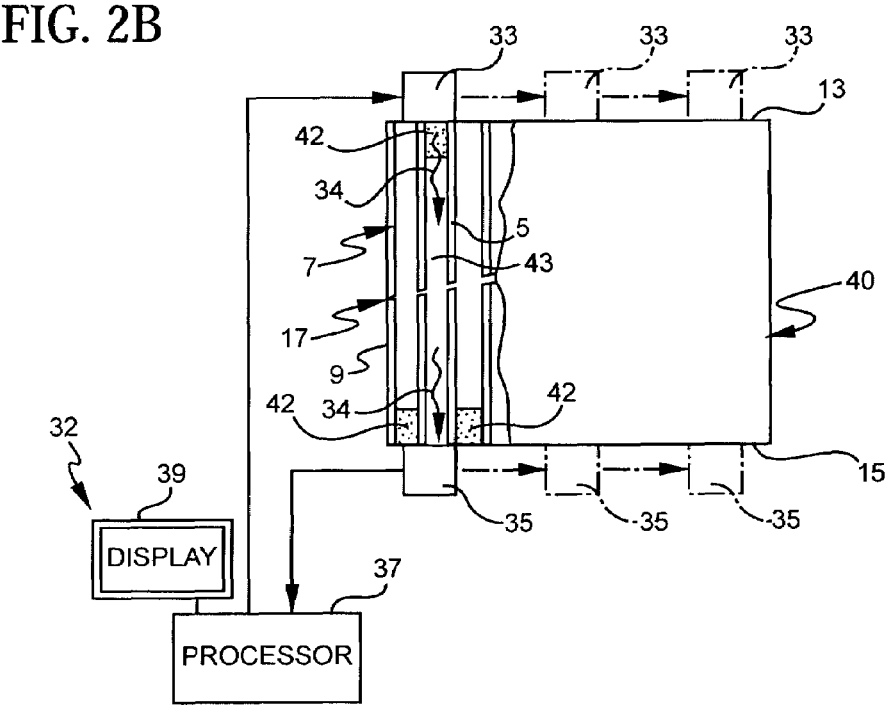
FIG. 2B is a schematic diagram of the contact through-transmission embodiment of the method as applied to a plugged substrate used as a particulate filter.

FIG. 2B illustrates the contact method of the invention as applied to a filter-type ceramic substrate 40. Such substrates 40 have end plugs 42 located at one end of each of the gas conducting cells 7 to define plugged passageways 43. The previously described mode of operation is also used here. Again, in this particular mode of the invention, the transmitting and receiving transducers 33, 35 are maintained in opposing relationship and sequentially relocated along a diameter or chord of the substrate 40, and sequentially actuated in order to produce a series of linear scans of the substrate 40.

Figure 2C:
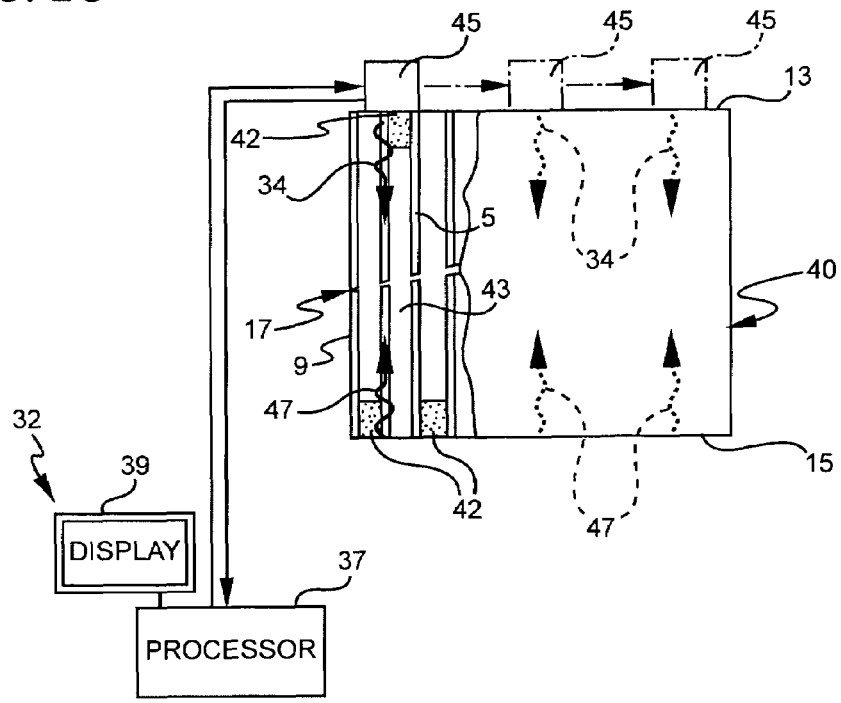
FIG. 2C is a schematic diagram of the pulse-echo embodiment of the method applied to a plugged ceramic substrate such as a particulate filter.

FIG. 2C illustrates an alternative embodiment of the method of the invention wherein the system 32 includes transmitting and receiving transducers which have been unitized into a single, ultrasonic transceiver 45 and a reflected echo of the wave is sensed. This mode is referred to herein as a "pulse echo" method. This particular embodiment of the method operates in "sonar" fashion, wherein the ultrasonic waves generated by the transceiver 45 are bounced off and reflected from the opposite end of the substrate 40. In this particular embodiment of the method, transmission is used wherein both the transmitted wave 34 and the reflected wave 47 are transmitted through the longitudinal web walls 5 of the substrate 40. In this embodiment of the method, the ultrasonic transceiver 45 placed in contact with the structure 40 at the inlet end 13 or outlet end 15 and is sequentially repositioned and re-actuated in much the same fashion as described with respect to the methods illustrated in FIGS. 2A and 2B such that a scan across the diameter or a chord of the substrate 40 is achieved. Discontinuities and/or inhomogenieties 17 such as internal cracks may be detected and located by the reflected echo using this pulse echo method. Moreover, internal homogeneities may be detected. This pulse echo method is equally applicable to filters 40 including plugs 42 as shown, but may be used for detecting discontinuities and inhomogenieties 17 in flow-through substrates as well.

The method illustrated in FIGS. 2A, 2B and 2C may be implemented by commercially available ultrasonic testing equipment (such as model number EPOCH 4 PLUS series, manufactured by Panametrics-NDT of Waltham, Mass.). Gains from 20-80 dB, preferably 40-60 dB, and filter settings of between about 100 KHz and 1 MHz and preferably 300 KHz to 800 KHz are utilized. The transmitters and receivers are preferably protective membrane transducers or dry-couplant transducers. Such transducers may have a compliant surface or elastomeric membrane which is placed in contact with the substrate. Optionally, a membrane may be placed in contact with the substrate and a gel may be applied between the membrane and a standard ultrasonic transducer used.

Figure 3A:
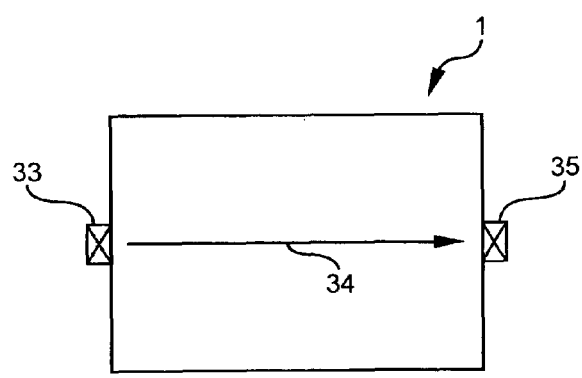
FIG. 3A is a schematic diagram illustrating the principle of the through-transmission embodiment of the method of the invention.
Figure 3B:
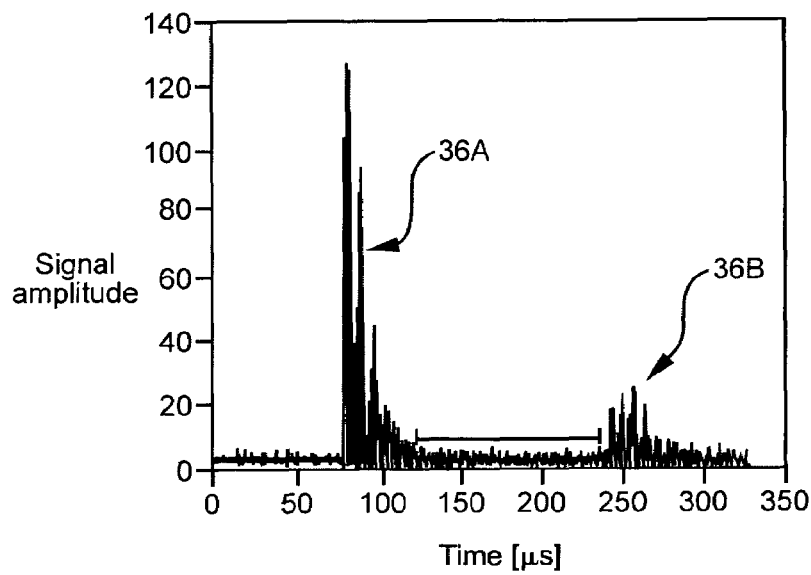
FIGS. 3B and 3C illustrate the amplitude of an ultrasonic through-wave transmitted through a substrate without internal discontinuities and a substrate with internal discontinuities, respectively.
Figure 3C:
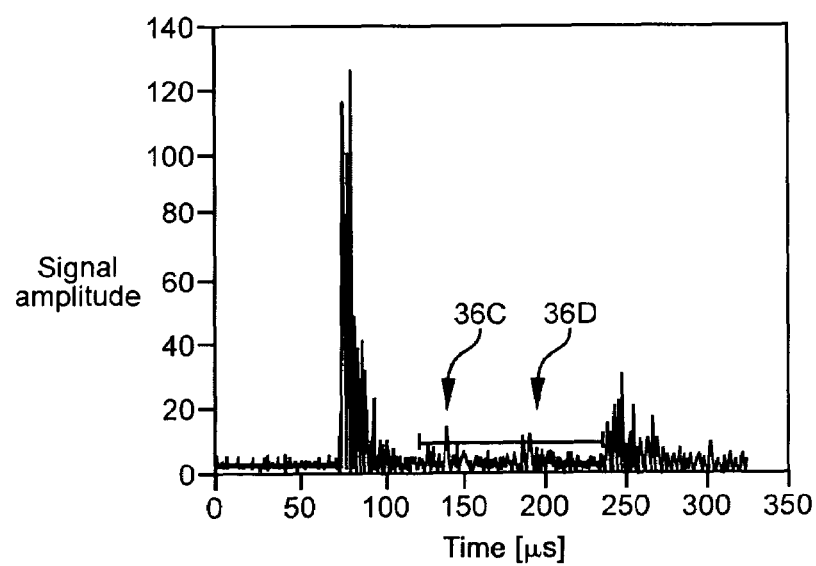
Figure 3D:
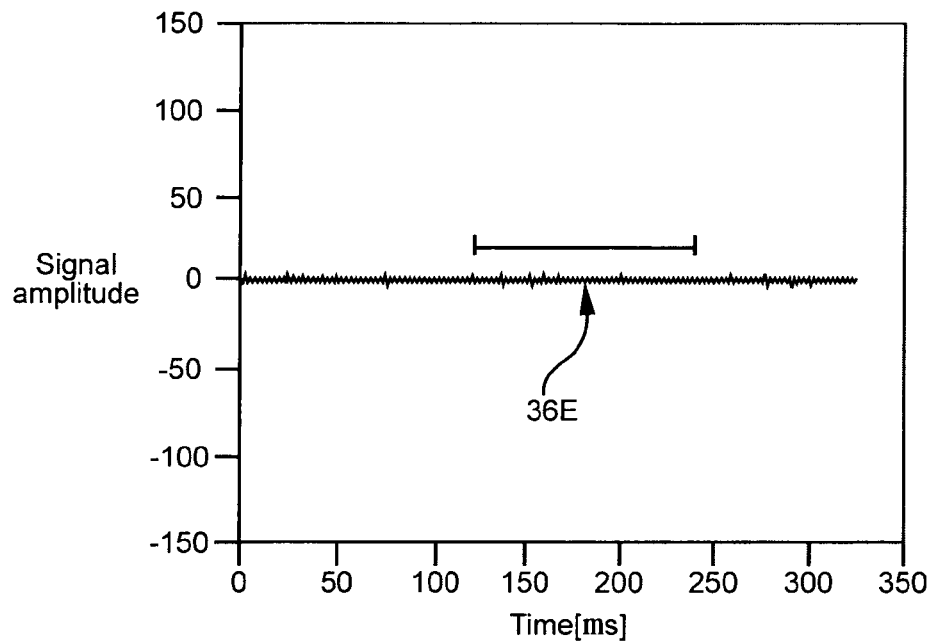
FIG. 3D illustrates the amplitude of an ultrasonic through-wave transmitted through a substrate with a large (blocking) internal discontinuity.

FIGS. 3A, 3B and 3C illustrate how the contact through-transmission embodiments of the method illustrated in FIGS. 2A and 2B operate. In particular, FIG. 3B is a graph of the amplitude of the ultrasonic wave 34 transmitted lengthwise through a substrate 1 when no discontinuity is present. As is schematically illustrated in FIG. 3A, when the transmitting transducer 33 is actuated to generate an ultrasonic wave 34, the wave is transmitted through the entire length of the substrate 1. Hence, the receiving transducer 35 registers a relatively high amplitude pulses 36A, 36B (FIG. 3B) when it receives the slightly attenuated wave 34. By contrast, when a small crack or discontinuity is present along the path between the transmitting and receiving transducers 33, 35, the trace produces in the time gate one or more peaks 36C, 36D. In that case where a significant crack or discontinuity is present in the substrate 1, as is illustrated in FIG. 3D, no high-amplitude pulse of the ultrasound wave is received or registered by the receiving transducer 35. Instead, the electric signal 36E generated by the receiving transducer 35 remains flat as shown. Hence, a flat line in the trace indicates a significant internal cracks or other defect within the substrate 1 at that tested location. Of course, by retesting at many other locations, an image of the respective tests may be assembled which provides a spatial image of any defect present.

Figure 4A:
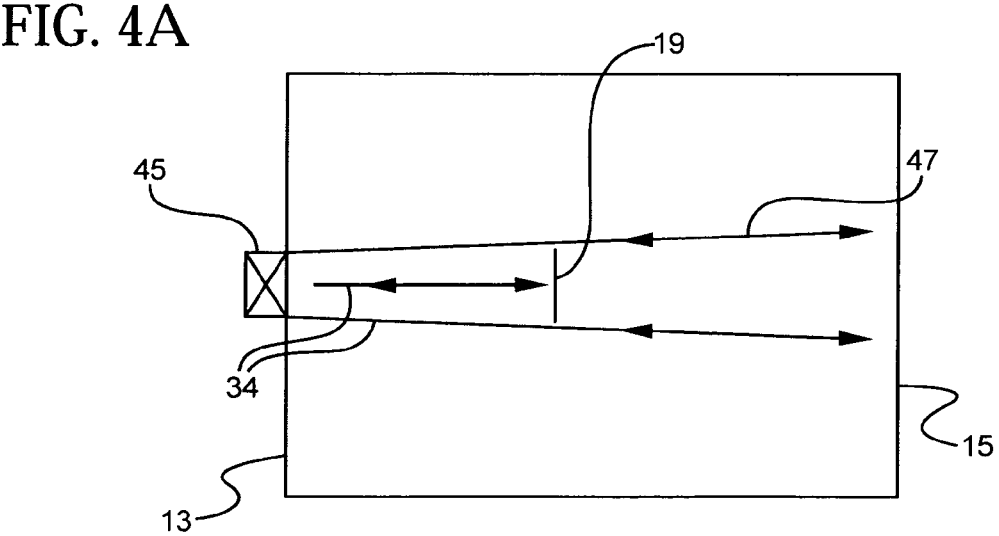
FIG. 4A is a schematic diagram illustrating the principle of the pulse echo embodiment of the method of the invention.
Figure 4B:
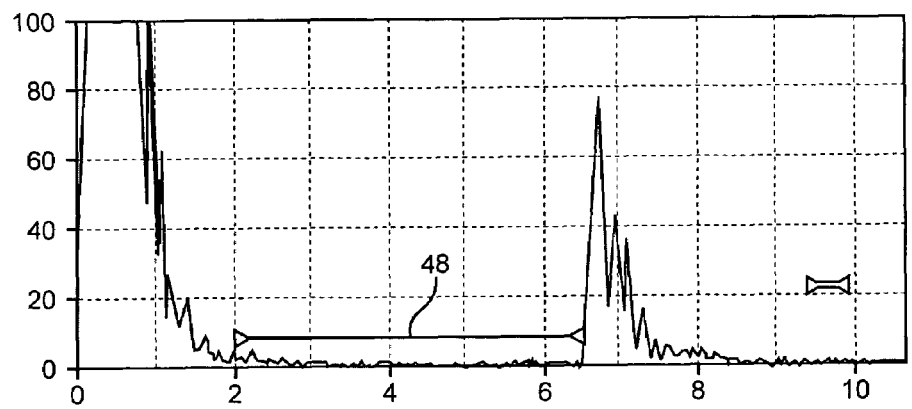
FIG. 4B is a graphical trace illustrating changes in the amplitude of a pulse echo over time for a crack-free diesel particulate filter substrate.
Figure 4C:
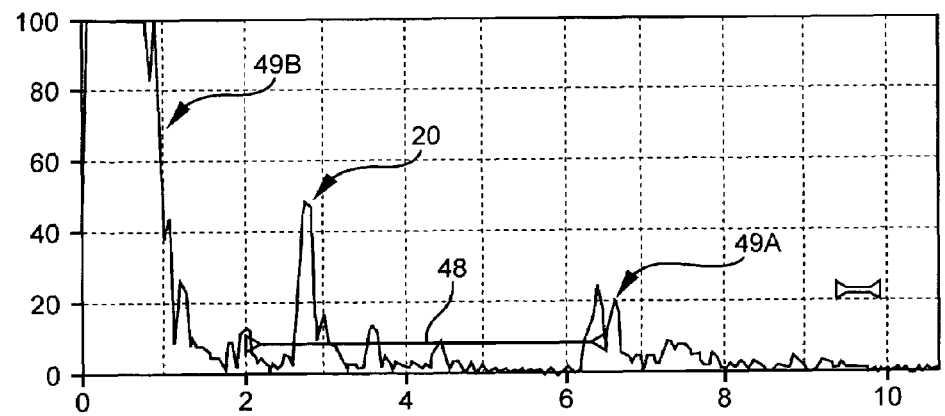
FIG. 4C is a graph illustrating changes in the amplitude of a echo over time for a diesel particulate filter having a crack.

FIGS. 4A, 4B and 4C illustrate how the pulse-echo embodiment of the method illustrated in FIG. 2C operates. When the ultrasonic transceiver 45 generates a pulse 34 of ultrasonic sound, it is transmitted from the inlet end 13 of the substrate 1 through the web walls, where it is reflected at the substrate-air interface defined by the outlet end 15. If there is no discontinuity (e.g., a crack) in the path of the wave 34, the only reflected wave 47 received by the transceiver 45 is the one reflected off the back wall of the substrate defined in this example by the outlet end 15. FIG. 4B illustrates a graphical trace of the amplitude of the received signal versus time with no cracking being evident. In particular, no peaks are evident within the time gate 48. However, when an internal crack or other discontinuity 19 is present in the pathway of the ultrasonic wave or pulse 34, the resulting reflected wave 47 generates an additional spike 20 in amplitude within the trace within the time gate 48, as is illustrated in FIG. 4C. Specifically, the reflected wave 47 generates a backwall spike 49A near the end of the graph from the ultrasonic echo reflected from the back wall of the honeycomb substrate, as well as a main bang spike 49B disposed at the left side of the graph which is indicative of reflection off the inlet face 13. One advantage of this pulse echo embodiment of the invention is that the location of the crack 19 along the axis of rotation of the cylindrical substrate 1 can be substantially determined. The relative location of the defect 19 is determined by the relative location of peak 20 within the time gate 48. In the case where a ring-off crack or discontinuity is sufficiently large, it may completely block the incident ultrasonic wave. In this instance, the reflected wave 47 may only generate the echo from the crack and no "backwall" echo such that the amplitude of backwall peak 49A will be on the order of background noise.

FIGS. 5A, 5B and 5C schematically illustrate the pulse echo signatures associated with different patterns of cracks or other types of discontinuities that may be present in a ceramic honeycomb substrate 1. FIG. 5A is the schematic equivalent of the pulse echo signature illustrated in FIG. 4C, wherein a single spike 20 is generated between the "main bang" pulse 49B of the ultrasonic transducer 45 and the back wall echo pulse 49A at the left and right sides of the graph, respectively. It is indicative of a single crack 19 in the honeycomb substrate 1. FIG. 5B illustrates how two different spikes 20a, 20b are generated by two different cracks 19a, 19b which are not aligned with one another along the axis of rotation of the ceramic honeycomb substrate 1. The relative amplitude of the peaks is indicative of the relative size of the two cracks 19a, 19b. Further, sonar principles can be used not only to determine the relative positions of the cracks 20a and 20b along the axis, but their absolute position as well. Their position is correlated to the relative position of the peaks 20a, 20b to the peaks 49A, 49B. Finally, FIG. 5C illustrates that, in the rare instance where a relatively larger crack 19c eclipses a smaller crack 19d along the axis of the honeycomb substrate 1, that the signature of the smaller crack 19d can be masked by the signature of the larger crack. Normally, such masking will not pose a problem in practice, as the presence of a single substantial discontinuity is sufficient for a substrate to be rejected during a quality control inspection. However, if avoidance of such undesirable masking is necessary, such avoidance may be accomplished by scanning the substrate 1 along two axes, instead of only one, i.e., from the other end.

Figure 6A:
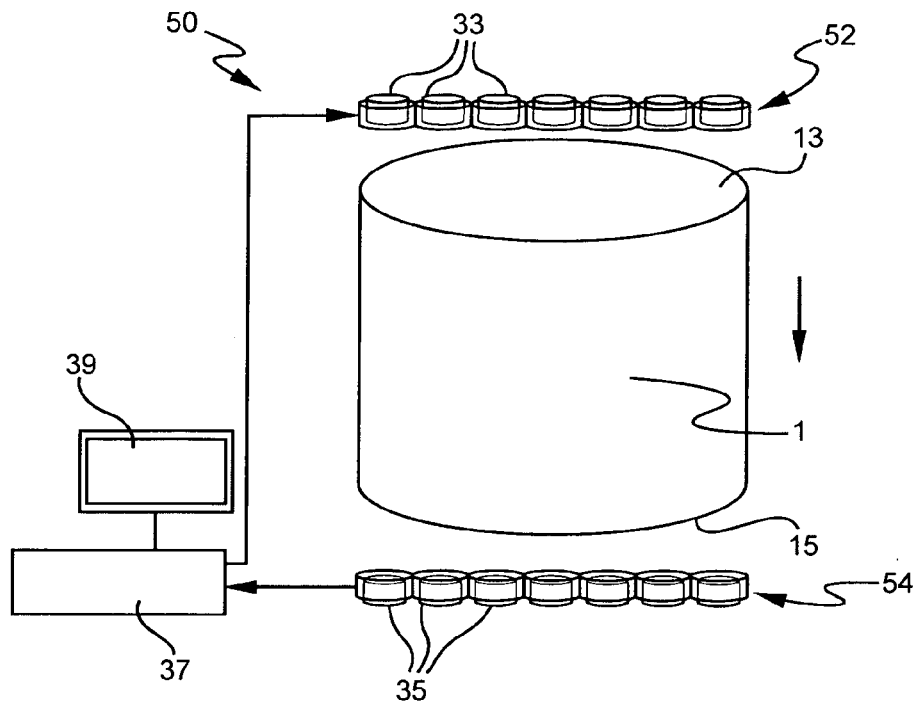
FIG. 6A is a schematic diagram of a first embodiment of the non-contact apparatus of the invention having opposing linear arrays of transmitting and receiving ultrasonic transducers for implementing a non-contact embodiment of the method.

FIG. 6A illustrates a first embodiment 50 of an apparatus of the invention which may be used to carry out the non-contact method of the invention. The method and apparatus are designed to rapidly scan the entire cross-section of a ceramic honeycomb substrate 1 in a non-contact method in a search for internal defects or inhomogenieties. The apparatus 50 includes an array or row 52 of transmitting transducers 33, arranged in opposing relationship relative to an array or row 54 of receiving transducers 35. In operation, there is relative movement between the ceramic honeycomb substrate and the upper and lower arrays 52, 54 of transmitting and receiving transducers while, at the same time, the upper row 52 of transducer transmitters periodically and simultaneously transmits waves 34 of ultrasonic pulses. For the configuration of FIG. 6A, the relative movement is in the direction into and out of the paper in successive increments wherein a new pulse is generated for each increment in the scan. The row 54 of receivers receives these waves and converts them into an electric signal which is in turn conducted to a digital processor 37. Processor 37 in turn generates a plurality of parallel graphs which together, create a complete scan of the honeycomb substrate 1 over its entire cross-section, which may then be displayed on monitor 39. In a preferred embodiment, the ceramic substrate 1 may be moved relative to the rows 52, 54 of transducer transmitters and receivers via a conveyor belt (not shown). The array of transmitters 52, 54 are preferably as large as the width of the honeycomb substrate 1, such that one sweep can provide suitable complete screening of the substrate. Of course, a smaller array may be employed with repositioning after each sweep to provide complete scan coverage.

Figure 6B:
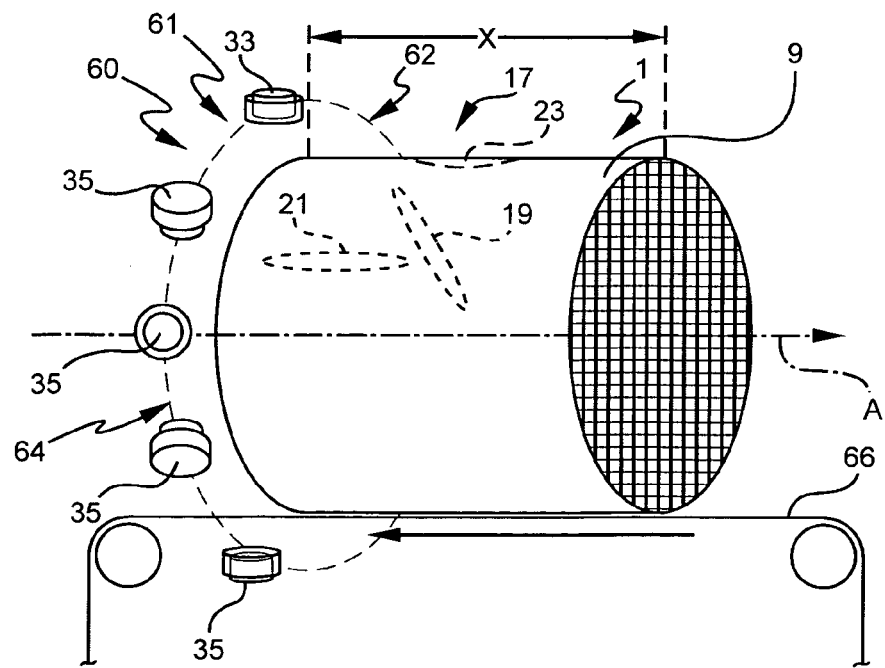
FIG. 6B is a schematic diagram of a second embodiment of the non-contact apparatus of the invention having a circular array of transmitting and receiving ultrasonic transducers for implementing a non-contact embodiment of the invention, and further illustrating the operation of this embodiment.

FIG. 6B illustrates a second embodiment 60 of the apparatus of the invention that implements a non-contact embodiment of the inventive method, which comprises an array of transducers 61 positioned radially outward from the skin 9 of the circumferential periphery of the honeycomb substrate 1, and preferably arranged in a circular pattern. The arrays 61 are preferably positioned along semicircles 62, 64 and the array 61 may include, for example, four transducer transmitters 33, and four transducer receivers 35 arranged in opposing pairs. Preferably, the transmitters 33 are positioned in the first semicircle 62, and the four receivers 35 are positioned in the second semicircle 64. The electrical inputs and outputs of the transducer array 61 are connected to a processor and display which, for simplification purposes, is not shown in FIG. 5B. In operation, a ceramic honeycomb substrate 1 is moved through the array 61 via a conveyor belt 66 as shown such that the honeycomb substrate 1 is diametrically scanned through its circumference throughout its entire length X to determine the presence of an internal discontinuity 17, such as ring-off crack 19, an axial crack 21, and/or a skin separation 23. Of course the number of pairs may be increased or decreased depending on the size of the honeycomb substrate 1 or resolution desired. This method and apparatus may also be utilized to inspect a dried green honeycomb structure, such as a honeycomb log which includes two or more uncut lengths of the honeycomb structure therein.

Figure 6C:
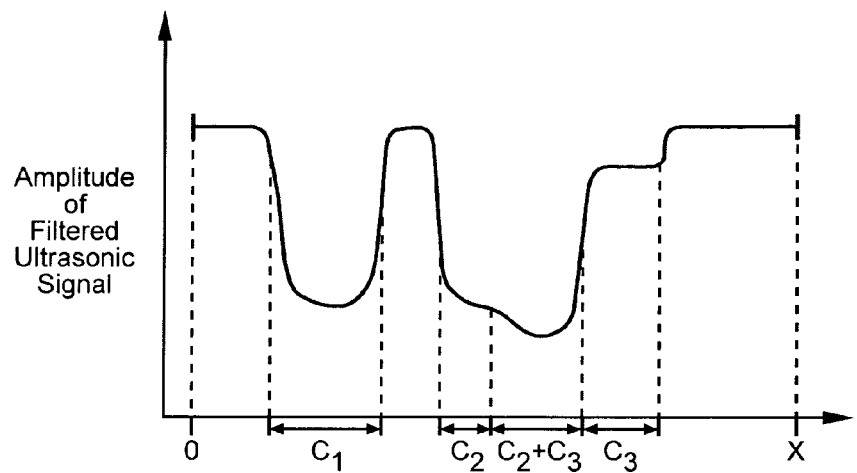
FIG. 6C is a graph illustrating variations in the amplitude of the ultrasonic signal generated by the array of FIG. 6B over the length X of a substrate containing internal discontinuities.

FIG. 6C schematically illustrates the combined output of the transducer array 61 relative to the longitudinal axis of the honeycomb substrate 1. At section C1 of the graph, the portion of the honeycomb substrate 1 having an axial crack 21 is disposed within the transducer array 61, thereby attenuating the combined amplitude of the ultrasonic signal generated by the array. The amplitude rises again to the upper base line indicative of a normal internal structure until the transducer array 61 is disposed around the ring-off crack 19, and skin separation 23. As is indicated in FIG. 6C, the combined amplitude of the signal transmitted by the transducer array 61 falls in area C2 as the array is aligned with the ring-off crack 19, and falls further in the area C2+C3, where the transducer array 61 simultaneously circumscribes both the ring-off crack 19, and the skin separation 23. Amplitude rises again in area C3 when the array is disposed only around the skin separation 23, and then resumes to its normal baseline for the balance of the axial length X of the substrate once the circular transducer array 61 gets past the end of the skin separation 23.

Figure 7:
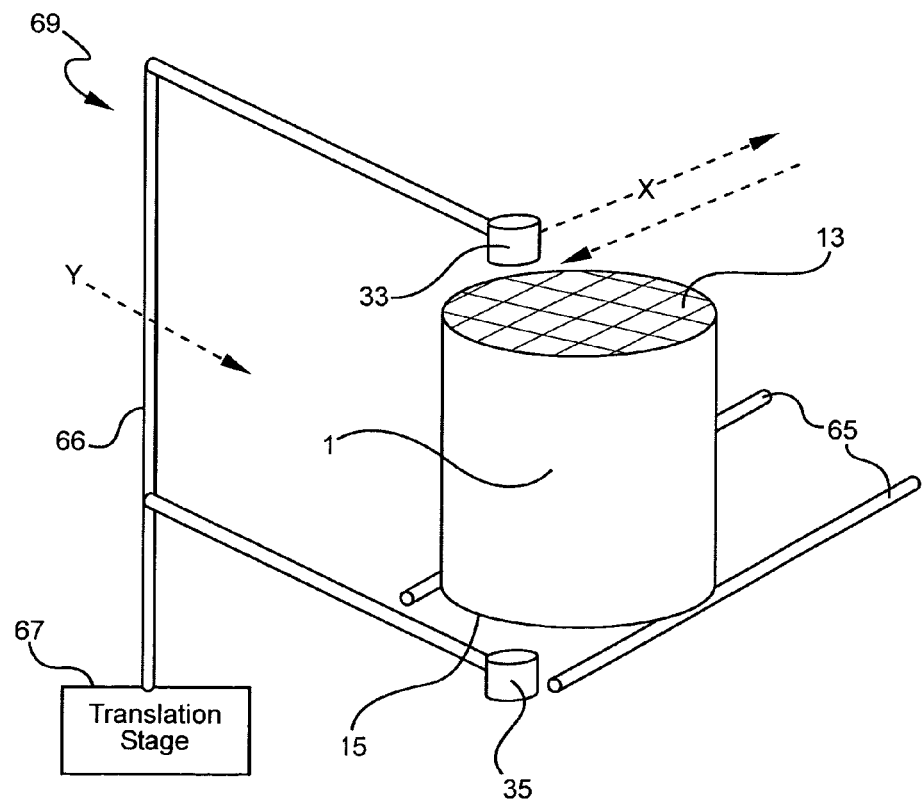
FIG. 7 is a schematic diagram of an embodiment of the non-contact test apparatus of the invention wherein two opposing ultrasonic transducers are simultaneously scanned across the ends of the substrate to detect discontinuities.

FIG. 7 schematically illustrates a third embodiment 69 of the apparatus of the invention that implements the non-contact inventive method. In this embodiment 69, the honeycomb substrate 1 is mounted on a suitable stationary platform 65, which may include two rails or other suitable fixturing, such that the inlet face 13 and the outlet face 15 are exposed. Transducer transmitter 33 and transducer receiver 35 are positioned at opposing ends of the honeycomb substrate 1 and adjacent to the inlet face 13 and outlet face 15. The transducers should be arranged in close proximity to the substrate 1, preferably near the ends 13, 15. Standoff distance between transducers 33, 35 and substrate 1 is preferably between about ½ inch (about 13 mm) to about 2 inches (about 51 mm). Both transducers 33, 35 may be mounted on a mechanical support system 66 that maintains their opposing position with respect to each other. Mechanical support system 66 may be connected to a translation stage 67 that controls the position of the transducers 33, 35 along the X and Y coordinates. From a predetermined home position the translation stage 67 may be raster scanned by actuating the stage to move the transducers 33, 35 along the X axis at a rate of about 0.01 to about 0.1 inch per second (about 0.025 mm/s to about 2.5 mm/s), and at about 0.03 to about 0.1 inch (about 0.76 mm to about 2.5 mm) increments. After the transducers 33, 35 have traversed a distance equal to or greater than the diameter of the honeycomb substrate 1, the translation stage 67 may be incremented forward at about 0.03 to 0.1 inch (about 0.76 mm to about 2.5 mm) and the process of moving across the X axis is repeated. This process continues until the entire face 13, 15 of the honeycomb substrate 1 has been scanned. The length of both the X and Y increments, and the rate of the stage movement is dependent on the required resolution.

Figure 9A:
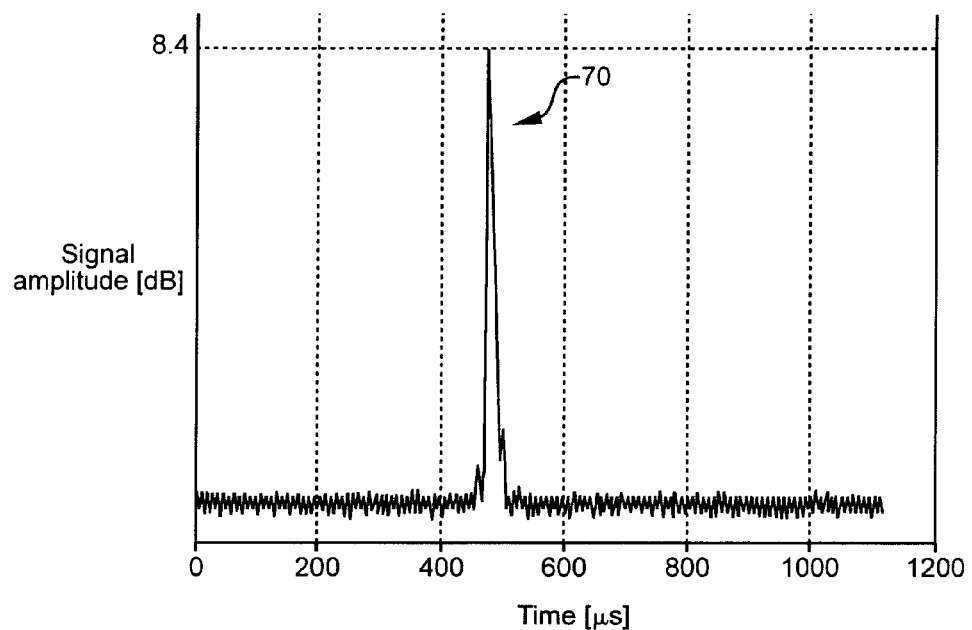
FIGS. 9A and 9B are traces illustrating signals generated from of the embodiment of the non-contact test apparatus of FIG. 7 for a flow-through-substrate.

The operational method for the apparatus of FIG. 6A and FIG. 7 for flow through substrates is described with reference to FIG. 8. In operation, the transducer 33 transmits an ultrasonic wave into the air space 26a between the honeycomb substrate 25 and the transducer 33, which subsequently travels into the substrate 25. The test frequency of the wave may be at 100 KHz-1 MHz, preferably 150-700 KHz. Because of the cellular structure of the substrate 25 there are two paths, one through the air in the air passageways 27 and one through the substrate wall 5. Because the speed of sound is drastically different in the air (i.e., about 340 m/s) in the passageways 27 versus the longitudinal substrate walls 5, the processor 37 may be programmed with a targeted "gate" in the time domain to differentiate the two paths (through air 34 and through substrate wall 34') to inspect the substrate. FIG. 9A illustrates the resultant trace of the signal amplitude versus time in open air (with no substrate in the test apparatus) and shows the DTA peak 70 which is reflective of the extent of distance L (FIG. 8) between the two transducers 33, 35. The time-of-flight (TOF) for the DTA peak is given by:

$$TOF_{DTA} = L/Cair$$

Where Cair is the speed of sound in air.

Figure 9B:
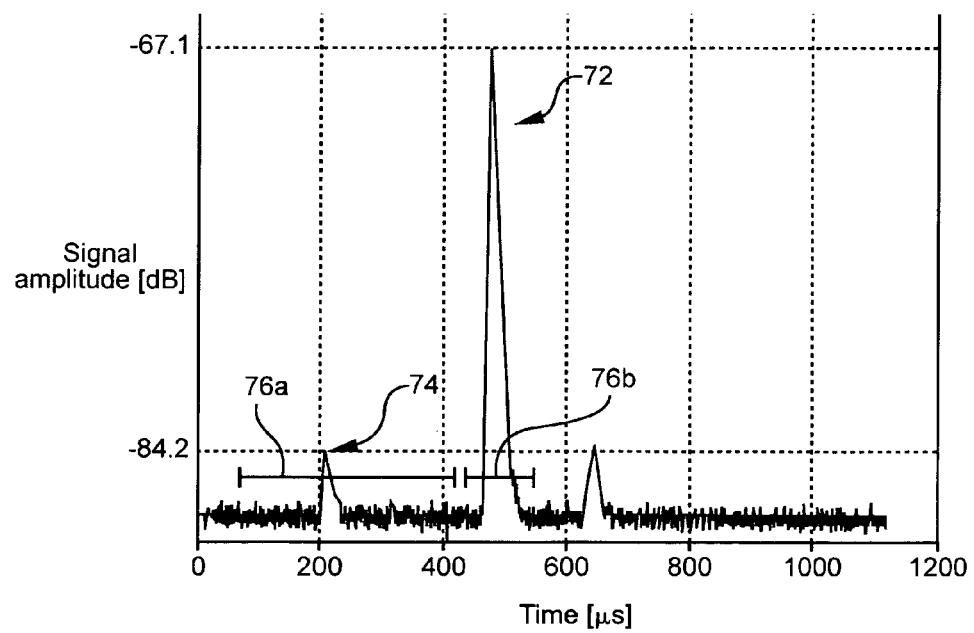

FIG. 9B illustrates the resultant trace of the signal amplitude versus time with a substrate positioned in the test apparatus. The distance H in FIG. 8 is the respective height of the substrate 25. In the trace of FIG. 9B, a modulated DTA peak 72 is shown as well as DTS peak 74. The reduced DTA peak 72 has a reduced amplitude but generally occurs at the same time as peak 70 (FIG. 9A). The time-of-flight (TOF) for the DTS peak 74 is given by:

$$T_{DTS} = (L-H)/Cair + (H/Cmat)$$

Where Cmat is the ultrasonic velocity of the substrate.

Because the speed of sound through air and through the material of the wall are dramatically different, the peaks 72, 74 will be well separated in time. To interpret the data of the traces, gates 76a, 76b may be positioned to select either the DTA signal 72 or DTS signal 74. In a honeycomb substrate inspection method, the DTS signal 74 may be used in constructing a raster scan image indicative of the discontinuity, for example. When measuring ring-off cracks or other discontinuities of the web across the axis of rotation of the structure 25, the DTS image may yield better representation of the internal defects or inhomogenieties.

Figure 10A:
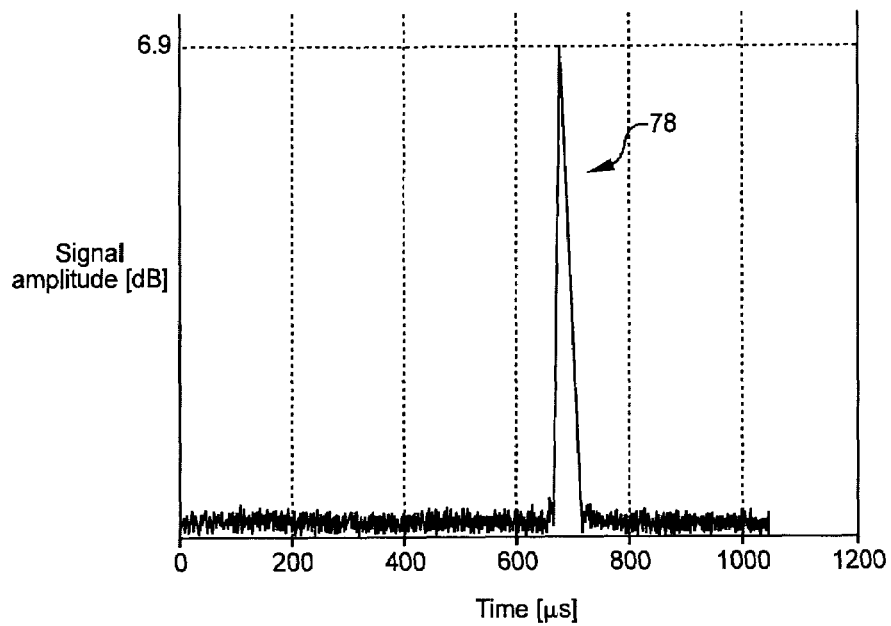
FIGS. 10A and 10B are traces illustrating signals generated from of the embodiment of the non-contact test apparatus of FIG. 7 for a honeycomb filter.
Figure 10B:
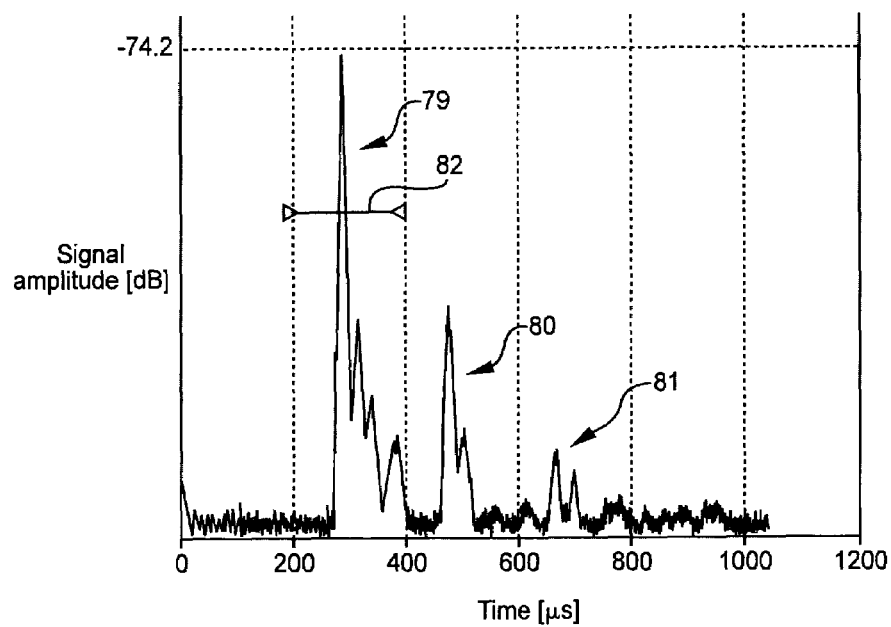

FIGS. 10A and 10B illustrate the resultant traces of signal amplitude versus time with (FIG. 10B) and without (FIG. 10B) a plugged honeycomb filter positioned in the test apparatus. FIG. 10A illustrates the resultant trace of the signal amplitude versus time in open air (with no filter in the test apparatus) and shows the open air peak 78 which is reflective of the extent of the stand off distance L (FIG. 8) between the two transducers 33, 35. In the trace of FIG. 10B, a DTS peak 79 is shown. Peaks 80 and 81 are multiple reflections from the end of the filter and may be effectively ignored. The DTS peak 79 has an amplitude which may change at various positions depending on the presence or absence of the discontinuities or inhomogenieties in the filter. For the non-contact method and apparatus, the system used must be non-contact ultrasonic test system, for example as available from VN Instruments, model SIA7 and Ultran, model iPASS. Single element transducer pairs or arrays may be used also. In the non-contact case, a broader frequency range may be employed. For example, the actuation frequency for the transducer may be between 150 KHz and 1.5 MHz, and more preferably between 200 KHz to 700 KHz.

Figure 11:
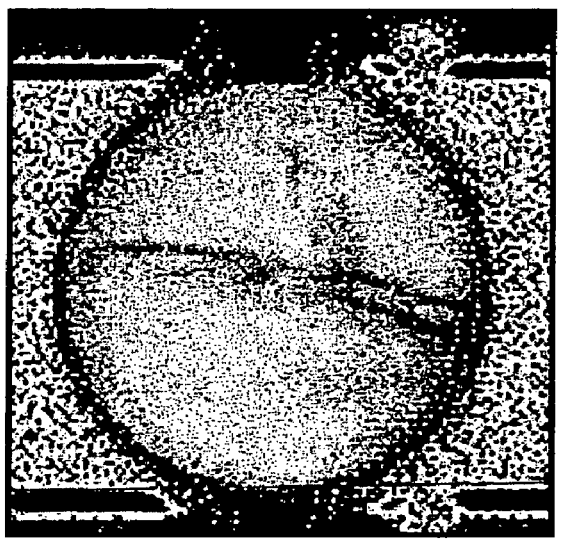
FIGS. 11 and 12 are raster scan images of the IR and TOF images, respectively, according to embodiments of the non-contact test method.
Figure 12:
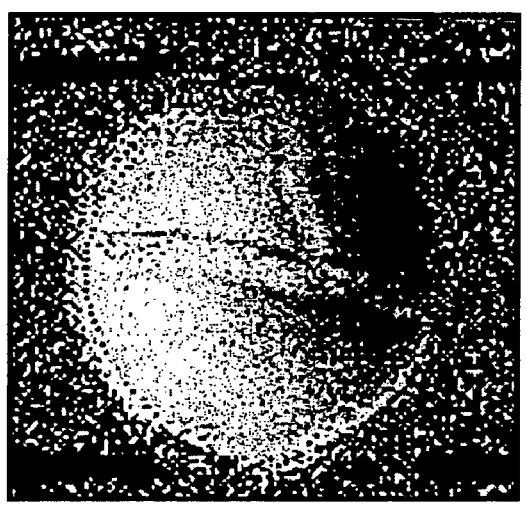

After the completion of the raster scan there may be two images created. One is an image representative of the variations of the integrated response (IR) or signal strength of the DTS signal in the substrate. The other is an image representative of the variations of the TOF of the DTS signal in the substrate. Within the raster scan image, a pattern will be developed which is indicative of an internal discontinuity or internal inhomogeniety. FIG. 11 illustrates a raster scan IR image of the DTS strength showing the presence of a branched axial crack, for example, in a cordierite honeycomb substrate having a 600/4 geometry. FIG. 12 illustrates a raster scan TOF image also showing the presence of the same branched axial crack, for example.

In the case when the DTS signal is too weak, the DTA signal 72 may be selected by the gate 76 and the same procedure described above may be employed. The relative strength of DTA vs DTS signal from the same substrate is affected by the cell density, i.e., 900/2 vs. 400/6 or 600/4, of the substrate, and the operating frequency of the ultrasonic transducer. In other words, the acoustic wavelength in air relative to the cell size and cell wall thickness affects the wave propagation, i.e., the DTS 74 or DTA 72. The best testing frequency, therefore, needs to be adjusted based on the product by performing optimizing experiments in the frequency ranges listed herein.

Because of the inherent limit of non-contact ultrasonic testing, i.e., significant acoustic impedance mismatch between air and the solid, the DTS signal is, in general, quite weak. In order to provide a sufficient signal-to-noise ratio for the DTS signal, it is preferable to have multiple signal averaging at each scan location. The resultant raster scan image, i.e., the IR or TOF image, will then more readily reveal the subtle features (cracks and/or inhomogenieties). The presence or absence of the revealed features (cracks and/or inhomogenieties) may be verified by the use of pulse echo method or through transmission methods defined herein. Accordingly, combinations of the method described herein may be utilized.

Figure 13A:
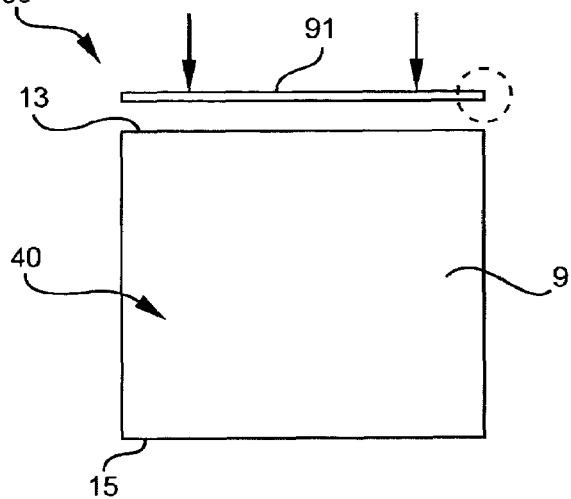
FIGS. 13A-13D are schematic diagrams illustrating both a system and method of the invention wherein a membrane is first placed in contact with a surface of the honeycomb structure, a gel coupling compound is next applied to the membrane, and an ultrasonic transceiver is then slidably scanned over the structure in engagement with the membrane in a predetermined pattern.
Figure 13B:
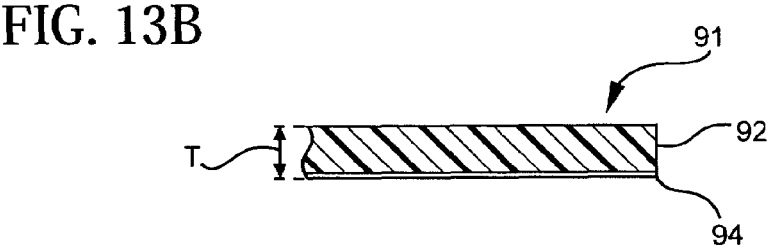

With reference now to FIGS. 13A and 13B, the system 90 of the invention includes a membrane 91 which is placed in contact with a surface 13 of a honeycomb ceramic structure 40. The membrane 91 preferably has an acoustic impedance that is at least within about 20% of the geometric mean of the acoustic impedance of the ceramic honeycomb structure 40 and a front end of the ultrasonic transceiver 45 that engages the membrane, and more preferably an acoustic impedance that is exactly or very close to the aforementioned geometric mean in order to minimize attenuation of the ultrasonic waves emitted by the transceivers 45 of the system 90, and the resulting reflected waves 47. The membrane should also have a thickness T that is approximately one-quarter wavelength of the ultrasonic radiation emitted by the transceivers 45 in order to further minimize signal attenuation. Finally, the membrane 91 should be easy to mount in position over the surface 13 and easy to remove when the scanning operation is completed, and should not be absorbent to gel coupling compound. To these ends, as shown in FIG. 8B, the membrane 91 in the preferred embodiment of the system 90 consists of a sheet of polyester 92 having a layer 94 of temporary adhesive on one side that has a thickness T of less than 5.0 mils; or even about 2.0 mils. A membrane 91 having all of the aforementioned properties is commercially available from C-Line Products located in Chicago, Ill. and sold under the registered trademark "Cleer-Adheer". Such sheet material may easily be cut to fit the shapes of the various surfaces of a ceramic honeycomb structure 40, and the temporary adhesive present on one side of such sheet material makes it easy to temporarily affix over such a surface 13 in intimate, uniform contact without the presence of air bubbles or other irregularities that can generate noise in both the transmitted and reflected ultrasonic waves 34, 47. The temporary adhesive on such sheet material further makes it easy to peel off after the scanning operation is completed.

Figure 13C:
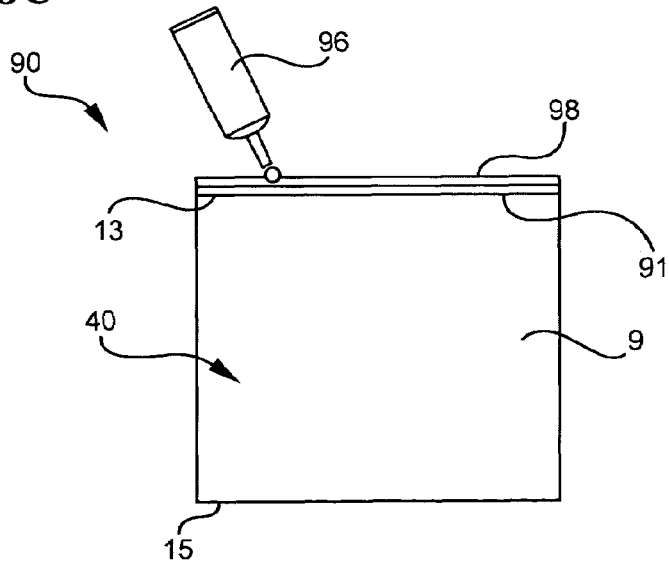
Figure 13D:
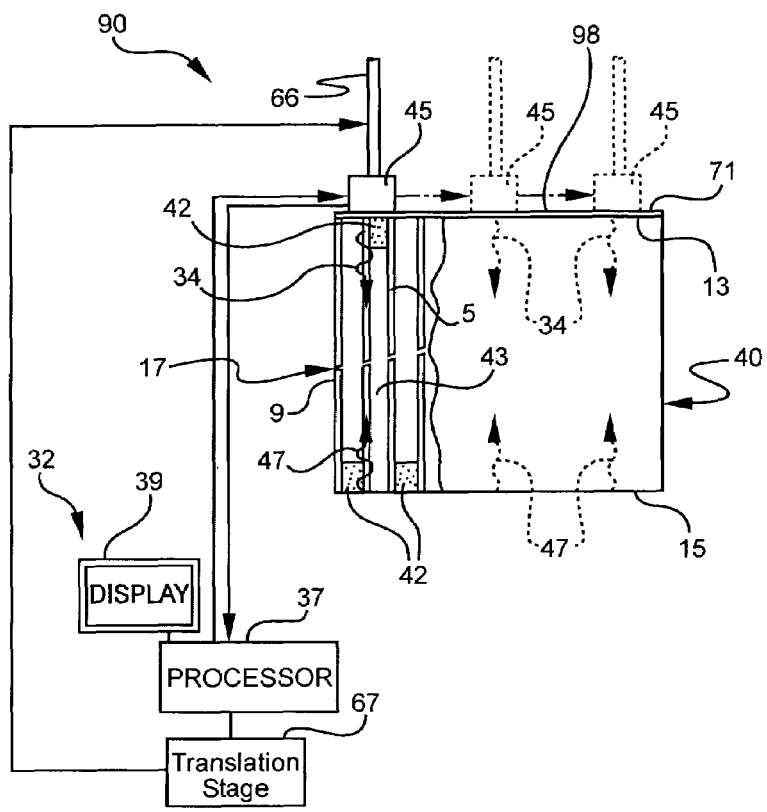

With specific reference now to FIGS. 13C and 13D, the system 90 of the invention further includes a layer of acoustic gel coupling compound 98 applied over the outside surface of the membrane 91 after it has been placed in contact with the surface 13 of the ceramic honeycomb structure 40. Such compounds are commercially available and may be applied to the membrane 91 via an applicator 96 as shown. FIG. 13D illustrates all of the primary components of the system 90 in operation. After the membrane 91 and layer 98 of acoustical gel coupling compound have been applied to a selected surface 13 of a ceramic honeycomb structure 40, an ultrasonic transducer 45 which is connected to a support 66 of a translation stage 67 is slidably moved in engagement with the membrane in a predetermined pattern over the surface 13 of the structure 40. In this system 90, the ultrasonic transceiver may be the combination of a type-V601 transducer having a 1 inch diameter and a center frequency rating of 0.5 MHz connected to a Panametrics-brand model "Epoch 4" flaw detector. The operation of the translation stage 67 and the periodic pulsing of the transceiver 45 is coordinated by the digital processor 37 such that the periodic generation of the transmitted waves 34 occurs simultaneously with the scanning movement of the transceiver 45. In the preferred embodiment, the transceiver is moved at a rate of about 0.901 inches per millisecond and is engaged with a uniform pressure over the membrane 91, and may be actuated between about 10 and 30 times during the scan (depending upon the size of the ceramic honeycomb structure 40) to construct a sufficiently accurate and complete ultrasonic image. The processor 37 may operate the ultrasonic transceiver at a gain level of about 50.3 dB. Such a continuous operation is substantially faster than a "stop-and-go" operation where the transceiver 45 is not actuated until it is stopped at a desired location, and is made practical by the combination of the membrane 91 and layer 98 of gel coupling, which acts as a lubricant in addition to an ultrasonic coupling medium.

Figure 14A:
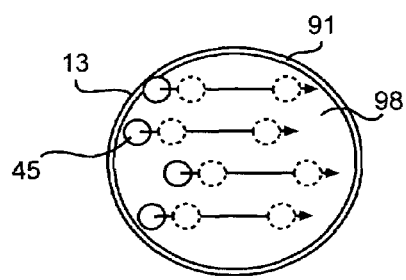
FIGS. 14A and 14B illustrate two possible pre-determined patterns that the translation stage moves ultrasonic transceiver illustrated in FIG. 13D.
Figure 14B:
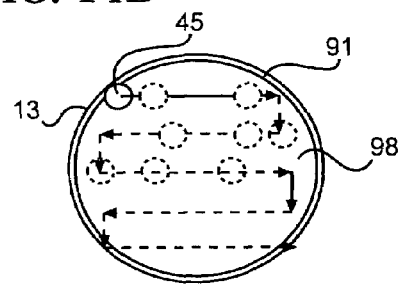

FIGS. 14A and 14B illustrate two different kinds of predetermined scanning patterns that the transceiver 45 may be moved in incident to implementing the method of the invention. FIG. 14A illustrates how the translation stage 67 can move the transceiver 45 in multiple linear, parallel passes over the surface 13. Alternatively, FIG. 14B illustrates how the translation stage 67 can move the transceiver in a raster scan pattern. While a single transceiver 45 has been illustrated, multiple transceivers may of course be used in order to expedite the scanning operation.

Figure 15A:
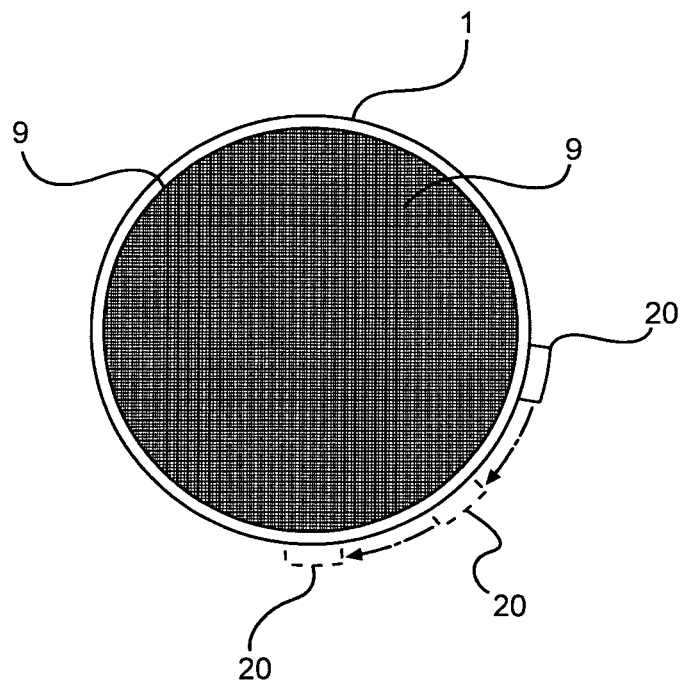
FIGS. 15A and 15B illustrate two additional pre-determined patterns where the translation stage moves the ultrasonic transceiver over the membrane applied to the surface.
Figure 15B:
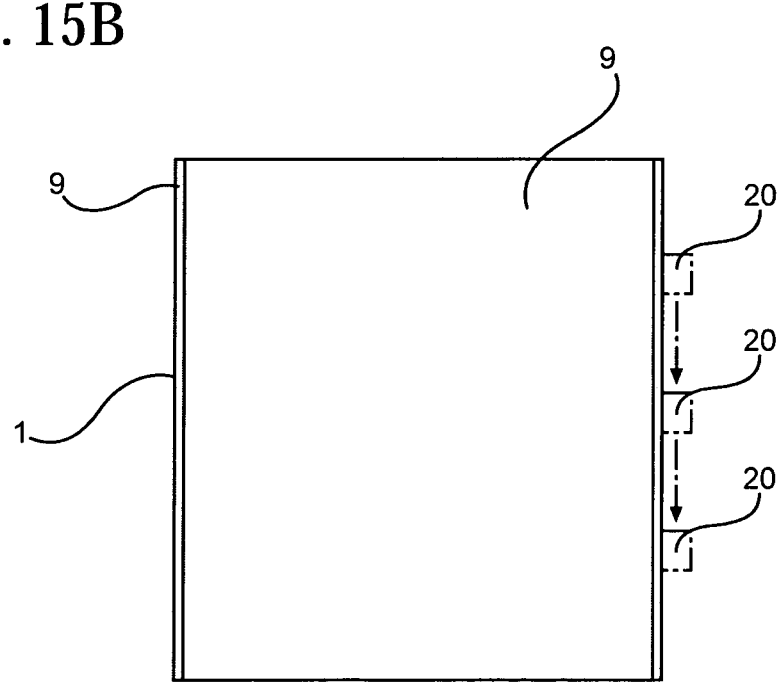

FIGS. 15A and 15B illustrate additional configurations for axial crack detection in ceramic honeycomb structures of the type used in diesel and automotive exhaust systems. In the configuration of FIGS. 15A and 15B, the membrane 91 is applied on the side skin of the honeycomb particulate filter 98, for example. The transducer or transducer array, e.g., a phase array transducer 201 may then slid both along the membrane surface in the radial direction, as shown in FIG. 15A, and along the axial direction, as shown in FIG. 15B, to detect axial cracks of unknown orientation. It is desired that ultrasonic couplant is applied between the transducer or transducer array 201 and the membrane surface 13 to effectuate efficient energy coupling. The transducer or transducer array 201 may have a slight curvature formed on its contact surface such that the contour thereof fits tightly to the outer skin contour of the honeycomb 98 through the membrane surface 13. The curvature can be either designed into the transducer or transducer array 201 itself, or alternatively, a transducer wedge (not shown in FIG. 15A or B, but widely used in ultrasonic testing) with the proper curvature fitting the honeycomb radius can be employed. The use of the wedge allows the use of a flat-bottom transducer or transducer array 201.

While the invention has been described with respect to several preferred embodiments, various modifications and additions will become evident to persons of skill in the art. All such additions, variations and modifications are encompassed within the scope of the invention, which is limited only by the appended claims, and equivalents thereto.

What is claimed is:

1. A system for detecting internal discontinuities and/or inhomogeneities in a green or fired ceramic honeycomb structure, comprising:
    a membrane disposed on a surface of the honeycomb structure;
    at least one ultrasonic transmitter engaged with said membrane and which transmits ultrasonic waves into the honeycomb structure;
    a translation assembly causing the at least one ultrasonic transmitter to slide on said membrane in a predetermined pattern; and
    an ultrasonic receiver that receives a modulated response from the ultrasonic waves transmitted into the honeycomb structure.

2. The system defined in claim 1, further comprising a gel coupling compound applied to the membrane that facilitates slidable movement and acoustical coupling of said at least one ultrasonic transmitter to said honeycomb structure.

3. The system defined in claim 1, wherein said membrane exhibits an acoustic impedance that is within about 20% of the geometric mean of the acoustic impedance of the ceramic honeycomb structure and the acoustic impedance of a front end of said at least one ultrasonic transmitter that engages said membrane.

4. The system defined in claim 1, wherein said membrane has a thickness that is approximately one quarter of the wavelength of the ultrasonic waves transmitted by the at least one ultrasonic transmitter.

5. The system defined in claim 1, wherein said membrane is a flexible sheet material.

6. The system defined in claim 5, wherein said flexible sheet material includes a sheet of polymeric material.

7. The system defined in claim 5, wherein said polymeric material is polyester.

8. The system defined in claim 5, wherein said flexible sheet material includes a layer of adhesive such that the flexible sheet material is detachably adherable on said surface of said honeycomb structure.

9. The system defined in claim 5, wherein said flexible sheet material is less than 5 mils thick.

10. The system defined in claim 1, where the at least one ultrasonic transmitter and the ultrasonic receiver is an ultrasonic transceiver that simultaneously operates in a pulse-echo mode while being slidably moved across said membrane.

11. A method for detecting internal discontinuities and/or inhomogeneities in a green or fired ceramic honeycomb structure, comprising the steps of:
    applying a membrane to a surface of the honeycomb structure;
    sliding an ultrasonic transmitter over the membrane and transmitting ultrasonic waves into the honeycomb structure;
    receiving a response of the transmitted ultrasonic wave as modulated by the structure; and
    constructing an image of internal discontinuities and/or inhomogeneities of said honeycomb structure based on said response.

12. The method defined in claim 11, wherein said membrane is applied by detachably adhering the membrane to a surface of the honeycomb structure.

13. The method defined in claim 11, further comprising the step of applying a coupling compound to the membrane prior to sliding the ultrasonic transmitter of the membrane.

14. The method defined in claim 11, wherein the ultrasonic transmitter is an ultrasonic transceiver that is operated in a pulse echo mode.

15. The method defined in claim 11, wherein the ultrasonic transmitter is moved in a predetermined pattern.

16. The method defined in claim 15, wherein the ultrasonic transmitter is moved in a raster scan pattern.

17. The method defined in claim 15, wherein the ultrasonic transmitter is moved in a pattern of linearly passes on the membrane covering the surface of the honeycomb structure.

18. The method defined in claim 11, wherein said ultrasonic waves are transmitted frequencies between about 200 kHz and 1 MHz.

19. The method defined in claim 18, wherein the ceramic honeycomb structure is formed from a porous cordierite ceramic, and wherein said ultrasonic waves are transmitted at frequencies between about 200 kHz and 600 kHz.

20. The method defined in claim 11, wherein a plurality of ultrasonic transmitters are moved on the membrane covering said surface of said honeycomb structure while transmitting ultrasonic waves into the honeycomb structure.

21. The method defined in claim 11, wherein the membrane is applied to an end face of the honeycomb structure.

22. The method defined in claim 11, wherein the membrane is applied to the side face of the honeycomb structure.

* * * * *